United States Patent
Hwang et al.

(10) Patent No.: US 7,507,819 B2
(45) Date of Patent: Mar. 24, 2009

(54) METHOD FOR PREPARING AMINO PHOSPHATE COMPOUNDS

(75) Inventors: Kuen-Yuan Hwang, Hsinchu Industrial District (TW); An-Bang Duh, Hsinchu Industrial District (TW); Chih-Fu Chen, Hsinchu Industrial District (TW); Cheng-Jung Chiang, Hsinchu Industrial District (TW)

(73) Assignee: Chang Chun Plastics Co., Ltd., Taipei (TW)

( * ) Notice: Subject to any disclaimer, the term of this patent is extended or adjusted under 35 U.S.C. 154(b) by 380 days.

(21) Appl. No.: 11/269,320

(22) Filed: Nov. 7, 2005

(65) Prior Publication Data

US 2007/0049753 A1    Mar. 1, 2007

(30) Foreign Application Priority Data

Aug. 30, 2005  (TW) ............................... 94129630 A

(51) Int. Cl.
    *C07D 251/54*  (2006.01)
(52) U.S. Cl. ..................................... 544/200
(58) Field of Classification Search .................. 544/200
    See application file for complete search history.

(56) References Cited

U.S. PATENT DOCUMENTS

| 3,920,796 A |   | 11/1975 | Sheridan |         |
|-------------|---|---------|----------|---------|
| 5,338,787 A | * | 8/1994  | Giroldini et al. | 524/100 |
| 6,008,349 A |   | 12/1999 | Suzuki et al. |      |
| 6,733,697 B2 | * | 5/2004  | Rhodes et al. | 252/606 |

FOREIGN PATENT DOCUMENTS

JP    11-130413 A    5/1999

* cited by examiner

*Primary Examiner*—Rei-tsang Shiao
(74) *Attorney, Agent, or Firm*—Morrison & Forester LLP

(57) ABSTRACT

The present invention relates to a method for preparing amino phosphate flame retardants. Melamine and phosphoric acid substances are used as a starting material, AND then the starting material reacts in the absence of solvents at a temperature ranging from 40 to 200° C. to obtain powdery amino phosphate compounds used as flame retardants. Since the reaction free of solvents is carried out under a condition of lower temperature, the powdery amino phosphate compounds can be obtained without drying steps. Therefore, not only the contaminations caused by solvent volatilization can be avoided, but also the process of preparing the product is simplified and the cost of the product is reduced.

9 Claims, No Drawings

METHOD FOR PREPARING AMINO PHOSPHATE COMPOUNDS

FIELD OF THE INVENTION

The present invention relates to methods for preparing amino phosphate compounds, and more particularly, a method for preparing amino phosphate compounds, in which melamine and phosphoric acid substances are used as a starting material.

BACKGROUND OF THE INVENTION

A flame retardant is a compound, which is added to base materials and can suppress base materials igniting or change burning properties of base materials. Currently, plastics, textiles, and coatings have been widely applied to building materials, interior decorating materials, electronic and electric devices, and communication products. However, these materials having poor igniting resistance usually cause significant loss of lives and wealth. Therefore, it becomes more and more important to utilize flame retardants.

In general, halogen-containing flame retardants are used, especially bromine-containing flame retardants. In order to reach the severe requirement for retarding flame, for example, UL 94V-0 grade, adjuvant agents, such as antimonous oxide, are employed. Since antimonous oxide is a carcinogen compound and such bromine-containing flame retardants release erosive bromide free radicals and hydrogen bromide gas, and toxic bromide volatiles after burning, those materials having bromine-containing flame retardants or antimonous oxide are really harmful to human bodies and environments.

Phosphorus-containing flame retardants are the most common used flame retardants to substitute the aforementioned bromine-containing flame retardants. For example, red phosphorus or other phosphorus-containing organic compounds are used as flame retardants. However, as these flame retardants are directly added to base materials, a high adding amount is needed in order to reach a certain flame retarding effect. Moreover, due to their low molecular weight and high migration, properties of base materials, such as electric properties, will be adversely affected.

Compared with phosphorus-containing flame retardants, amino phosphate flame retardants do not have the above-mentioned shortcomings. Generally, the conventional methods for preparing amino phosphate compounds include wet-type and dry-type methods. With respect to wet-type methods, reactants are fist dissolved in solvents and stirred to become solution or emulsion. Then, the solution or emulsion is heated to perform solvent reaction or emulsion reaction to synthesize a liquid product of a flame retardant. If a powdery product is requested, the liquid product is subjected to exclude solvents as disclosed in U.S. Pat. No. 6,008,349. During drying, several disadvantages are raised: the solvents remained in the flame retardant will produce stink and toxicity; energy and solvents will be consumed due to evaporating solvents by heat, resulting in higher process and product cost; and volatilization of solvents will cause environmental contaminations and healthy injuries, being adverse to production.

With respect to dry-type methods, the reactants are pulverized, mixed, calcined, cooled and granulated at a temperature from 300 to 400° C. to obtain the desired products as depicted in JP-A-H11-130413 and U.S. Pat. No. 3,920,796. However, they have drawbacks that the reactions must undergo high temperature process and the steps of preparations are complicated.

To overcome the above-mentioned problems, the present invention has been achieved after the inventors intensively study and make improvements.

SUMMARY OF THE INVENTION

It is a primary objective of the present invention to provide a method for preparing powdery amino phosphate flame retardants without using solvents.

It is another objective of the present invention to provide a method for preparing powdery amino phosphate flame retardants at low temperature.

It is still another objective of the present invention to provide a method for preparing powdery amino phosphate flame retardants by simple processes.

It is a further objective of the present invention to provide a method for preparing powdery amino phosphate flame retardants with low cost.

It is a further objective of the present invention to provide a method for preparing powdery amino phosphate flame retardants without drying steps.

It is a further objective of the present invention to provide a method for preparing powdery amino phosphate flame retardants having satisfactory dispersibility without the need of extra milling steps.

To achieve the above-mentioned and other objectives, melamine and phosphoric acid substances are used as a starting material in the present invention. Then, without the need of solvents, the starting material reacts in a ball mill reactor at a temperature of from 40 to 200° C. to obtain powdery amino phosphate compounds used as flame retardants. Since the reaction free of solvents in the present invention is carried out under a condition of low temperature from 40 to 200° C., the powdery amino phosphate compounds can be obtained without drying. Therefore, the synthetic steps of the products are simplified and the cost of the products is reduced.

DETAILED DESCRIPTIONS OF THE PREFERRED EMBODIMENTS

In the present invention, melamine and phosphoric acid substances are used as a starting material. Then, the starting material reacts in the absence of solvents in a ball mill reactor at a temperature ranging from 40 to 200° C. to obtain a powdery amino phosphate compound used as a flame retardant.

Examples of the phosphoric acid substances in the present invention include, but not limited to, phosphorus pentoxide, pyrophosphoric acid, polyphosphoric acid, phosphoric acid, phosphorous acid, hypophosphorous acid, phosphonic acid, phosphinic acid, phosphonous acid, hypophosphonous acid, and the like. Preferably, the phosphoric acid substances are phosphorus pentoxide and pyrophosphoric acid.

In the present invention, the molar ratio of melamine to phosphoric acid substances is in the range of 1:1 to 4:1. Preferably, the mol ratio is, but not limited to, 1~2:1.

In one embodiment, catalysts may also be used. Examples of the catalysts include, but not limited to, proton-donating Lewis acids, such as magnesium chloride, calcium acetate, antimony trioxide, tetraalkyltitanium, and the like. Among them, magnesium chloride is preferred. The catalysts added amount to 0 to 2.0% by weight based on the total weight of ingredients (including the melamine, the phosphoric acid substance and the catalyst) used in the reaction. It is preferred that the catalysts added amount to 0.1 to 1.0% by weight based on the total the total weight of ingredients used in the reaction.

In the present invention, melamine and phosphoric acid substances are added into a milling apparatus, then the milling apparatus is started after tightly closed. The temperature of the milling apparatus is maintained at 40 to 200° C. to react for 6 to 24 hours. Preferably, the temperature of the milling apparatus is maintained at a low temperature of 80 to 150° C. to react for 6 to 16 hours. After the milling apparatus is cooled, the powdery amino phosphate flame retardants are obtained.

In one embodiment of the present invention, a ball mill reactor is used as the milling apparatus to mill and heat reactants.

In the present invention, melamine and phosphoric acid substances used as a starting material are added into a milling apparatus and react directly in the absence of solvents to prepare powdery amino phosphate flame retardants. Accordingly, the powdery amino phosphate flame retardants with satisfactory dispersive properties can be directly obtained without drying steps, and thereby the present invention has advantages of simplifying processes and reducing cost.

The present invention will be further described in detail with reference to the following examples. These examples are merely to explain the features and effects of the invention, and do not to limit the scope of the invention.

EXAMPLES

Example 1

Under atmosphere, charged in a 5 L ball mill reactor were 141.94 g (1.0 moles) of diphosphorus pentoxide and 126.06 g (1.0 moles) of melamine (commercial name: Chang Chun Melamine), and the reactor was started after tightly closed and reacted at 150° C. for 16 hours. After the reactor is cooled, the powdery melamine phosphate product is obtained. The thermal degradation of the powdery product at 260° C. was measured with differential thermal/thermogravimetric analyzer. The loss of weight was 0.45% by weight. The results of phosphorus content and dispersibility of the powdery melamine phosphate product were shown as in Table 1.

Example 2

Under atmosphere, charged in a 5 L ball mill reactor were 70.97 g (0.5 moles) of diphosphorus pentoxide, 126.06 g (1.0 moles) of melamine (commercial name: Chang Chun Melamine) and 0.5 g of magnesium chloride catalyst, and the reactor was started after tightly closed and reacted at 100° C. for 6 hours. After the reactor is cooled, the powdery melamine phosphate product is obtained. The thermal degradation of the powdery product at 260° C. was measured with differential thermo/thermogravimetric analyzer. The loss of weight was 0.23% by weight. The results of phosphorus content and dispersibility of the powdery melamine phosphate product were shown as in Table 1.

Example 3

Under atmosphere, charged in a 5 L ball mill reactor were 88.99 g (0.5 moles) of pyrophosphoric acid, 126.06 g (1.0 moles) of melamine (commercial name: Chang Chun Melamine) and 0.5 g of magnesium chloride catalyst, and the reactor was started after tightly closed and reacted at 100° C. for 6 hours. After the reactor is cooled, the powdery melamine phosphate product is obtained. The thermal degradation of the powdery product at 260° C. was measured with differential thermo/thermogravimetric analyzer. The loss of weight was 0.43% by weight. The results of phosphorus content and dispersibility of the powdery melamine phosphate product were shown as in Table 1.

Comparative Example 1

Under atmosphere, charged in a twin-screw extruder were 70.97 g (0.5 moles) of diphosphorus pentoxide and 126.06 g (1.0 moles) of melamine (commercial name: Chang Chun Melamine), and a bar like product was formed at the extrusion temperature of 340° C. After being cooled, the bar like product is pulverized, thereby a powdery melamine phosphate product is obtained. The thermal degradation of the powdery product at 260° C. was measured with differential thermo/thermogravimetric analyzer. The loss of weight was 0.25% by weight. The results of phosphorus content and dispersibility of the powdery melamine phosphate product were shown as in Table 1.

TABLE 1

|  | Example 1 | Example 2 | Example 3 | Comparative example 1 |
| --- | --- | --- | --- | --- |
| Reaction temperature (° C.) | 150 | 100 | 100 | 340 |
| Content of phosphorus (%) | 15.7 | 15.7 | 14.44 | 15.7 |
| Loss of weight at 260° C. | 0.45 | 0.23 | 0.43 | 0.25 |
| Dispersibility | good | good | good | poor |

Compared with conventional dry-type methods reacting at high temperature to prepare bar like products, the reactions were performed at lower temperature in the present invent. Furthermore, the powdery products were obtained without further milling in the present invention and the dispersive properties of the powdery products prepared by the method of the present invention were superior to the products made by conventional dry-type method. Moreover, the present invention used no solvents, thus the contaminations caused by volatilization of solvents could be prevent. Therefore, the present invention has advantages of environmental protection and product cost.

The invention has been described using exemplary preferred embodiments. However, it is to be understood that the scope of the invention is not limited to the disclosed embodiments. On the contrary, it is intended to cover various modifications and similar arrangements. The scope of the claims, therefore, should be accorded the broadest interpretation so as to encompass all such modifications and similar arrangements.

What is claimed is:

1. A method for preparing amino phosphate compounds, comprising: providing melamine and a phosphoric acid substance as starting materials in a ball mill reactor, and reacting the starting materials in the absence of solvents at a temperature ranging from 40 to 200° C. and for at least 6 hours to obtain powdery amino phosphate compounds without drying wherein the phosphoric acid substance is selected from the group consisting of diphosphorous pentoxide, pyrophosphoric acid, polyphosphoric acid, phosphoric acid, phosphorous acid, hypophosphorous acid, phosphonic acid, phosphinic acid, phosphonous acid, and hypophosphonous acid.

2. The method of claim 1, wherein the starting materials are reacted in the absence of solvents at a temperature ranging from 80 to 150° C.

3. The method of claim 1, wherein a molar ratio of the melamine to the phosphoric acid substance is from 1:1 to 4:1.

4. The method of claim 3, wherein the molar ratio of the melamine to the phosphoric acid substance is from 1:1 to 2:1.

5. The method of claim 1, further comprising providing a catalyst, wherein the catalyst is a proton-donating Lewis acid selected from the group consisting of magnesium chloride, calcium acetate, antimony trioxide, and tetraalkyltitanium.

6. The method of claim 5, wherein the catalyst is magnesium chloride.

7. The method of claim 5, wherein the catalyst is present in an amount of 0 to 2.0% by weight based on a total weight of the melamine, the phosphoric acid substance and the catalyst.

8. The method of claim 7, wherein the catalyst is present in an amount of 0.1 to 1.0% by weight based on the total weight of the melamine, the phosphoric acid substance and the catalyst.

9. The method of claim 1, wherein the obtained powdery amino phosphate compounds serve as flame retardants.

\* \* \* \* \*